United States Patent
Knühl et al.

[11] Patent Number: 5,587,506
[45] Date of Patent: Dec. 24, 1996

[54] PREPARATION OF N-PROTECTED N-ALKYLATED AMINO ACIDS

[75] Inventors: Klaus Knühl, Limburgerhof; Ulrich Karl, Ludwigshafen; Stefan Müller, Speyer; Bernd de Potzolli, Bad Dürkheim, all of Germany

[73] Assignee: BASF Aktiengesellschaft, Ludwigshafen, Germany

[21] Appl. No.: 530,310

[22] PCT Filed: Oct. 22, 1994

[86] PCT No.: PCT/EP94/03480

§ 371 Date: Sep. 6, 1995

§ 102(e) Date: Sep. 6, 1995

[87] PCT Pub. No.: WO95/12574

PCT Pub. Date: May 11, 1995

[30] Foreign Application Priority Data

Nov. 2, 1993 [DE] Germany .................. 43 37 331.3

[51] Int. Cl.$^6$ .................................................. C07C 269/06
[52] U.S. Cl. ...................... 560/12; 560/24; 560/29; 560/32
[58] Field of Search ........................ 560/32, 12, 24, 560/29

[56] References Cited

FOREIGN PATENT DOCUMENTS 9006914  6/1990  WIPO.

OTHER PUBLICATIONS

Hlavacek, et al. Collect.Czech. Chem. Commun. 53(11A)2473–94 1988.
Marino, et al. J. Chem. Soc. Chem. Commun. No. 6, 357–58 1972.

*Primary Examiner*—Joseph Conrad
*Attorney, Agent, or Firm*—Keil & Weinkauf

[57] ABSTRACT

A process for preparing N-protected N-alkylated amino acids of the formula

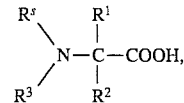

where $R^s$ and $R^1$–$R^3$ have the meanings indicated in the description comprises adding a compound of the abovementioned formula where $R^3$ is hydrogen to a solution of a base in a non-protic solvent and subsequently adding an alkylating agent.

4 Claims, No Drawings

PREPARATION OF N-PROTECTED N-ALKYLATED AMINO ACIDS

This application is a 371 of PCT/EP94/03480, filed Oct. 22, 1994.

The present invention relates to a novel process for preparing N-protected N-alkylated amino acids. N-Methylated amino acids are important constituents of peptides with high biological activity. Examples of such peptides are cyclosporins (Angew. Chem. 97 (1985) 88) and Dolastatins (Nat. Prod. 44 (1981) 482).

The preparation of N-monomethylated amino acids without using N-protective groups has achieved no practical importance. The processes described in the literature require the use of reagents which are costly and difficult to handle (methyl iodide, sodium hydride) in excess (Can. J. Chem. 55 (1977) 906). In addition, the esterification of the acid functionality which often occurs at the same time is unwanted and interfering (J. Org. Chem. 35 (1970) 1912).

N-Protected N-methylated amino acid derivatives are particularly advantageous for use in peptide chemistry because the methylated amino group is unable to react and the acid functionality does not have to be liberated. The most practicable process to date was introduced by Runge (WO 90/06914). In this case, t-butyloxy-carbonyl-protected amino acids are mixed with methyl iodide and the methylation takes place after addition of potassium tert-butanolate. However, both the chosen protective group and the methylating agent in the process described in WO 90/06914 are not optimal for preparing larger amounts of N-protected N-methylated amino acids. Use of the benzyloxycarbonyl protective group (abbreviated to Z hereinafter) in place of the t-butyloxycarbonyl protective group results in the desired N-alkylated amino acid in only very moderate yield besides many byproducts. Replacement not only of the protective group but also of the methylating agent (dimethyl sulfate in place of methyl iodide) results in no product being isolated.

We have found, surprisingly, that by changing the sequence of addition of the reagents and by changing the alkylating agent it is possible to prepare N-Z-protected N-alkylamino acids in very good yield and in high optical purity.

The present invention relates to a process for preparing N-protected N-alkylated amino acids of the formula I:

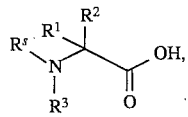

where $R^s$ is a conventional protective group for peptide synthesis, $R^1$ is the side chain of a proteinogenous amino acid or a functional derivative thereof, $R^2$ is hydrogen, $C_{1-6}$-alkyl, $C_{2-6}$-alkenyl, $C_{2-6}$-alkynyl or unsubstituted or $C_{1-4}$-alkyl-substituted phenyl or benzyl, and $R^3$ is methyl or ethyl, which comprises adding a compound of the formula II:

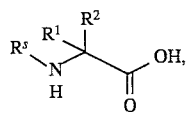

where $R^1$, $R^2$ and $R^5$ have the abovementioned meanings, to a solution of sodium or potassium tert-butanolate in a non-protic organic solvent and subsequently adding dimethyl or diethyl sulfate.

The process is suitable for preparing both the racemic compounds and the enantiomerically pure compounds.

Preferred meanings of the substituents in the formula I are:

$R^1$ the residue of a proteinogenous amino acid, in particular H, $C_{1-6}$-alkyl such as $CH_3$—, $CH_3$—$CH_2$—$CH_2$—, —$CH(CH_3)$—$CH_2$—$CH_3$, —$CH_2$—$CH(CH_3)_2$, $C_6H_5$—$CH_2$— and, very particularly, —$CH(CH_3)_2$.

$R^1$ radicals which may be mentioned for functional derivatives of proteinogenous amino acids are:

$CH_2$—$C_6H_4O$—$C(CH_3)_3$, —$CH_2$—$C_6H_4OCH_2$—$C_6H_5$, —$CH_2$—$O$—$CH_3$, —$CH_2$—$O$—$C(CH_3)_3$, —$CH_2$—$O$—$Si(CH_3)_3$, —$CH_2$—$O$—$CH_2$—$C_6H_5$, —$CH_2$—$C_6H_4O$—$Si(CH_3)_3$, —$CH(CH_3)$—$O$—$CH_3$, —$CH(CH_3)$—$O$—$C(CH_3)_3$, —$CH(CH_3)$—$O$—$Si(CH_3)_3$, —$CH(CH_3)$—$O$—$CH_2$—$C_6H_5$, —$CH_2$—$S$—$C(C_6H_5)_3$, —$CH_2$—$S$—$CH(C_6H_5)_2$, —$CH_2$—$S$—$CH_2$—$C_6H_5$, —$CH_2CH_2CH_2CH_2N$—$(CO)_2C_6H_4$, $R^2$ H, $C_{1-4}$-alkyl such as $CH_3$, —$CH_2$—$CH_3$, —$CH_2$—$CH_2$—$CH_3$, —$CH(CH_3)$—$CH_2$—$CH_3$, —$CH_2$—$CH_2$—$CH_2$—$CH_3$, —$CH_2$—$CH(CH_3)_2$, —$C(CH_3)_3$, $C_{2-4}$-alkenyl such as —$CH_2$—$CH=CH_2$, $C_{2-4}$-alkynyl such as —$CH_2$—$C\equiv CH$, or $C_6H_5$—, —$C_6H_4$—$CH_3$, $R^s$ benzyloxycarbonyl (=Z) or a protective group derived therefrom, preferably Z, DMZ (α,α dimethyl-benzyloxycarbonyl), BZ (4-brom-benzyloxycarbonyl), CZ (4-chlor-benzyloxycarbonyl), 3CZ (3-chlor-benzyloxycarbonyl), 2CZ (2-chlor-benzyloxycarbonyl), MOZ (4-methoxy-benzyloxycarbonyl), NZ (4-nitro-benzyloxycarbonyl), 2NZ (2-nitro-benzyloxycarbonyl), and AcOZ (4-acetoxy-benzyloxycarbonyl) und AcOZ (cf. Houben-Weyl: Methoden der organischen Chemie 4th Edition Volume 15/1 page 21). Z is particularly preferred.

The reaction according to the invention is expediently carried out under an inert protective gas such as helium or argon. Nitrogen is particularly advantageously used.

Suitable solvents for the reaction are non-protic solvents, in particular tetrahydrofuran, 1,2-dimethoxyethane, diethoxymethane, dioxane, dichloromethane, trichloromethane, carbon tetrachloride and N,N'-dimethylethyleneurea, N,N'-dimethylpropyleneurea and N-methylpyrrolidone. 1,2-Dimethoxyethane is preferably used.

Sodium t-butanolate or potassium t-butanolate is used as base. Potassium t-butanolate is preferably used. 2.2–10, preferably 3.5–6, equivalents of base are used based on compound II.

Dimethyl sulfate is preferably used as alkylating agent. 1.2–6, preferably 2.5–3.5, equivalents of alkylating agent are used based on compound II.

A polar protic additive is expediently added to the reaction mixture. This addition should take place no earlier than one hour but no later than 24 hours after addition of the alkylating agent is complete. Particularly suitable protic additives are water and alcohols such as methanol and ethanol. The amount of the additive is expediently 0.1–10, preferably 1–5, mole equivalents based on the starting material II. Water is particularly suitable as protic additive.

The reaction can be carried out at from −40° C. to +100° C., particularly advantageously from −10° C. to +20° C. The reaction mixture can be worked up by distillation, extraction, crystallization, chromatography or a combination thereof. Preferably, acidification is followed by extraction, and subsequently the compound I is crystallized.

Acids which can be used for the acidification are hydrochloric acid, sulfuric acid, phosphoric acid, hydrobromic acid, acetic acid and methanesulfonic acid. Sulfuric acid is preferably used. Extractants which can be used are solvents which are immiscible with water, such as pentane, hexane, heptane, octane, petroleum ether, ethyl acetate, diethyl ether, diisopropyl ether, methyl t-butyl ether, dichloromethane, chloroform, carbon tetrachloride, benzene, toluene and xylene, and toluene is particularly preferred. Crystallization can take place from organic solvents such as pentane, hexane, heptane, octane, petroleum ether, ethyl acetate, dichloromethane, chloroform, carbon tetrachloride, benzene, toluene, xylene, acetone, 2-butanone, methanol, ethanol, n-propanol, isopropanol, diethyl ether, diisopropyl ether, methyl t-butyl ether and mixtures thereof, and toluene and toluene/heptane mixtures are preferably used.

If the amino acids contain other reactive groups, such as cysteine, serine, tyrosine, lysine and threonine, these must be protected during the reaction.

The novel process has the following advantages:
1. It is possible to use starting materials which can be obtained straightforwardly and have advantageous handling properties (Z-amino acids, dimethyl sulfate),
2. there is no simultaneous esterification,
3. high yields are obtained,
4. a high-purity product which can be used without further purification for subsequent reactions is isolated,
5. no racemization occurs.

It is particularly surprising that the protic additive has beneficial effects on the purity and yield because experience has shown that such an additive tends to lead to incomplete reaction, racemization and transesterification.

EXAMPLES 1. (S)-Z-N-Methylphenylalanine 14.95 g of (S)-Z-phenylalanine were added to a solution of 25 g of potassium t-butanolate in 250 ml of dimethoxyethane at 0°–5° C. 18.9 g of dimethyl sulfate were added over the course of 45 min in such a way that the temperature remained at 0°–5° C. The mixture was then stirred at 0°–5° C. for 2 h and subsequently at 20° C. for 1 h. HPLC analysis showed a precursor/product ratio of 1:2.4. 2.5 ml of water were added, followed by 8.3 g of potassium t-butanolate (in 75 ml of dimethoxyethane). 6.3 g of dimethyl sulfate were metered in over the course of 15 min at 0°–5° C. The mixture was then stirred at this temperature for 2 h and subsequently at 20° C. for 2 h. HPLC analysis showed a precursor/product ratio of 1:69.2. The reaction was stopped by adding 500 ml of water. The organic phase was separated off, and the aqueous phase was extracted with 300 ml of toluene. The combined organic phases were discarded. The aqueous phase was acidified and extracted with toluene. The toluene phase was evaporated to dryness. The resulting crude product was recrystallized twice from toluene. 13 g of product with a purity>95% were isolated, m.p. 66°–67° C., $[\alpha]_D=-59.5°$ (c=1.0 in $CH_2Cl_2$).

The following were prepared as in Example 1:

2. (S)-Z-N-Methylvaline
   Yield: 85%, m.p. 69°–71° C., $[\alpha]_D=-84.6°$ (c=2.0 in $C_2H_5OH$)
   When this compound was prepared as in Example 1 but without addition of water before the addition of potassium t-butanolate the yield was 61%.

3. (±)-Z-N-Methylisoleucine
   Yield: 80%, m.p. 55°–56° C.
   When this compound was prepared as in Example 1 but without addition of water before the addition of potassium t-butanolate the yield was 65%.

4. (S)-Z-N-Methyl-O-t-butylserine
5. (S)-Z-N-Ethylphenylalanine
6. (S)-Z-N-Ethylvaline The following can be prepared in a similar way:
(S)-Z-N-Methylglycine, (S)-Z-N-methylalanine, (S)-Z-N-methyl-S-benzylcysteine; (S)-Z-N-methylleucine, (S)-Z-N-methylmethionine, (S)-Z-N-methyl-O-benzylthreonine.

We claim:

1. A process for preparing N-protected N-alkylated amino acids of the formula I

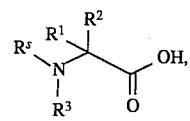

where $R^s$ is a conventional protective group for peptide synthesis, $R^1$ is the side chain of a proteinogenous amino acid or a functional derivative thereof, $R^2$ is hydrogen, $C_{1-6}$-alkyl, $C_{2-6}$-alkenyl, $C_{2-6}$-alkynyl or unsubstituted or $C_{1-4}$-alkyl-substituted phenyl or benzyl, and $R^3$ is methyl or ethyl, which comprises adding a compound of the formula II:

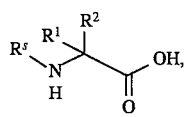

where $R^1$, $R^2$ and $R^5$ have the abovementioned meanings, to a solution of sodium or potassium tert-butanolate in a non-protic organic solvent and subsequently adding dimethyl or diethyl sulfate.

2. A process as claimed in claim 1, wherein potassium tert-butanolate is used as base and dimethyl sulfate is used as alkylating agent.

3. A process as claimed in claim 1, wherein potassium tert-butanolate is used as base and dimethyl sulfate is used as alkylating agent, and water is used as protic additive.

4. A process as claimed in claim 1, wherein an unsubstituted or substituted benzyloxycarbonyl radical is used as protective group $R^s$.

* * * * *